(12) United States Patent
Shaw et al.

(10) Patent No.: US 6,290,791 B1
(45) Date of Patent: Sep. 18, 2001

(54) METHOD OF MAKING A FLUID CONNECTION

(75) Inventors: John Edward Andrew Shaw, West Drayton; Chris Turner, Uxbridge; Anthony Robert Corless, Ash; John Robert Dodgson, Croydon, all of (GB)

(73) Assignee: Central Research Laboratories, Limited, Hayes (GB)

( * ) Notice: Subject to any disclaimer, the term of this patent is extended or adjusted under 35 U.S.C. 154(b) by 0 days.

(21) Appl. No.: 09/319,445

(22) PCT Filed: Dec. 4, 1997

(86) PCT No.: PCT/GB97/03363

§ 371 Date: Jul. 27, 1999

§ 102(e) Date: Jul. 27, 1999

(87) PCT Pub. No.: WO98/25065

PCT Pub. Date: Jun. 11, 1998

(30) Foreign Application Priority Data

Dec. 7, 1996 (GB) .................................................. 9625491

(51) Int. Cl.[7] .......................... B32B 31/28; B32B 31/24; C23C 16/04
(52) U.S. Cl. .................. 156/64; 156/275.7; 156/289; 156/293; 156/305; 156/308.2; 285/124.2; 285/124.4; 285/124.5; 427/255.6; 427/256; 427/423; 427/915
(58) Field of Search .................................... 156/64, 275.5, 156/275.7, 289, 293, 294, 305, 308.2, 324.4; 285/124.2, 124.3, 124.4, 124.5, 423, 915; 428/131, 137, 166, 167, 188, 192, 220; 204/451, 453, 601, 604; 427/255.6, 256

(56) References Cited

U.S. PATENT DOCUMENTS

| | | | |
|---|---|---|---|
| 4,390,575 | * 6/1983 | Kopp | 428/166 |
| 5,376,252 | * 12/1994 | Ekstrom et al. | 204/604 |
| 5,578,157 | * 11/1996 | Higdon | 156/294 |
| 5,779,868 | * 7/1998 | Parce et al. | 204/601 |
| 6,149,787 | * 11/2000 | Chow et al. | 204/601 |

* cited by examiner

Primary Examiner—Jeff H. Aftergut
Assistant Examiner—Michael A. Tolin
(74) Attorney, Agent, or Firm—William H. Bollman

(57) ABSTRACT

Apparatus comprising a micro engineered structure and a capillary or other tube and a method for connecting the tube to the structure. The micro engineered structure is composed of at least one substrate 2 in which fluid flow channels 6 are formed, connecting to an aperture 12 into which the tube 14 is inserted. A sealant material is flowed into the aperture around the tube and then hardened in order to seal the tube within the aperture.

20 Claims, 8 Drawing Sheets

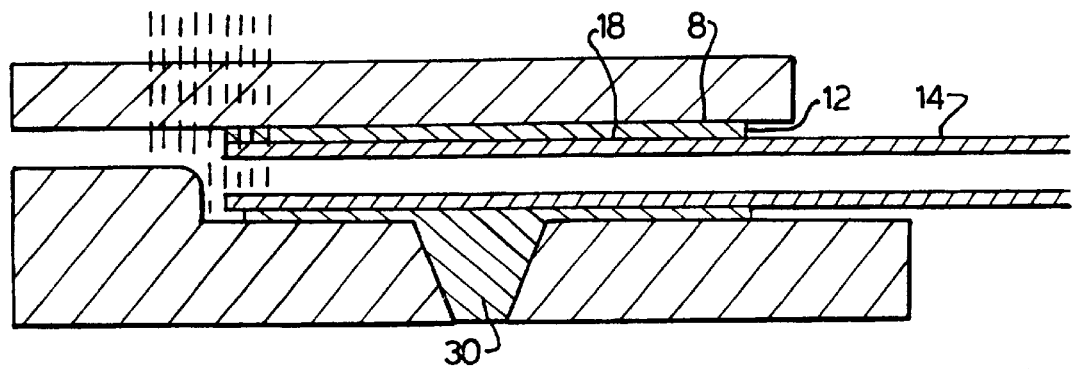
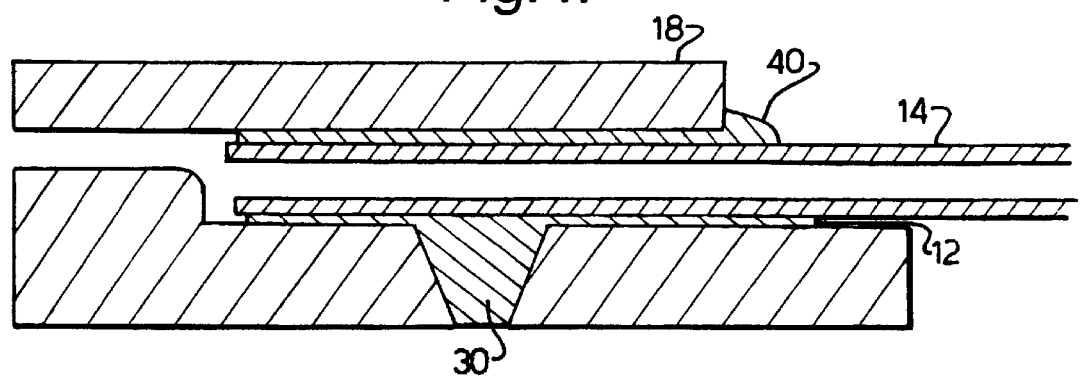

Fig.7.
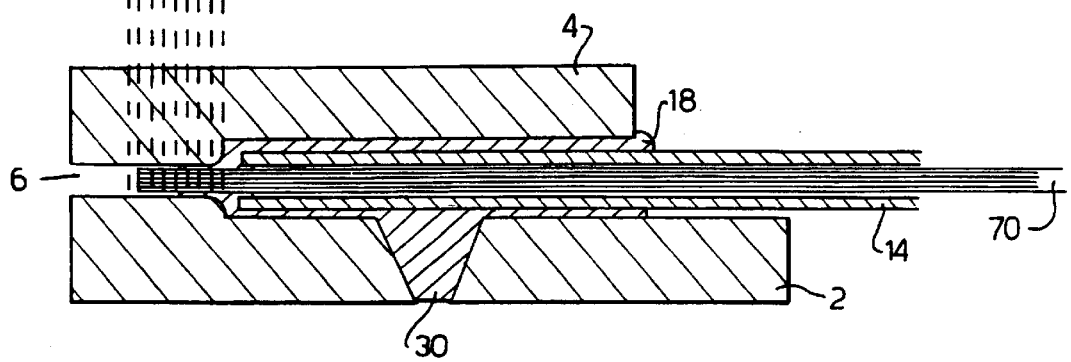
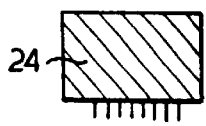
Fig.8.
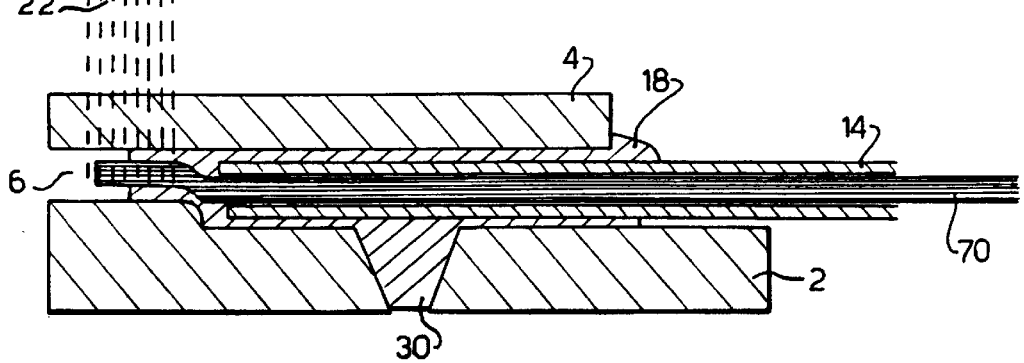
Fig.9.
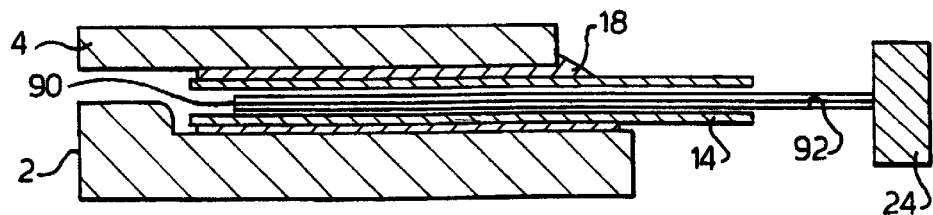

METHOD OF MAKING A FLUID CONNECTION

The present invention relates to fluid connections, in particular to a fluid connection between an inlet capillary or other small bore tube and a microengineered fluidic structure. Hereinafter the term "small bore tube" is taken to include capillary tubes and non-capillary tubes.

There is a growing interest in microengineered structures for transporting microscopic amounts of fluid, wherein the fluid is subject to chemical and/or biochemical processing and analysis. In particular our copending application WO96/12541 describes and claims method and apparatus for carrying out a diffusive transfer process between first and second immiscible fluids, wherein first and second flow paths communicate with one another in a region which is such as to permit the fluids to form a stable open interface therein, and wherein the flow paths in the interface region have a width normal to the interface within the range 10 to 500 micrometers. As described, the apparatus is typically constructed by etching grooves in the surface of a silicon sheet, to form fluid flow channels, and to bond a cover layer of glass onto the silicon sheet. However the application does not address in detail the problem of making an external connection to the microengineered device. It is desirable in this and many other applications of microfluidic devices, especially for analysis or where fluids within the devices are to be monitored or controlled, that connections be formed to external tubing without formation of excessive dead spaces or stagnant areas. This can require connection of the microfluidic device channels to capillary tubing of similar cross sectional dimensions.

Methods of making connections to capillary tubes are extremely well documented and are very diverse, depending on the specific application. For example, an end of the glass capillary may be surrounded by a plastic sheath for fixing securely in an inlet aperture of an apparatus, see for example EP-A-0698789 which describes a connection of capillary tubing to high pressure liquid chromatography apparatus. However, making a force fit with a flexible sheath or other insert would not be suitable for such a delicate microengineered structure as described in our above copending application. Further conventional connector structures for connection to circular cross section capillary tubes by conventional procedures require structures with a recess of circular cross section, sometimes tapered, which are generally unavailable with microengineered devices, and generally with dimensions greater than the thickness of substrates conventionally used for construction of microengineered structures. For the purposes of the specification, microengineered structures is intended to mean structures formed with one or more than one stacked substrates, each substrate being of generally planar form and of a thickness preferably 2 mm or less, and having fluid flow channels formed therein, at least parts of such channels having a cross-sectional diameter less than 1000 micrometers. It will be understood that diameter is intended to mean the thickness or width for non-circular cross sectional channels. It will further be appreciated that such channels may be extended in specific regions to form chambers etc. within the structure with dimensions greater than 1000 micrometers. The substrates are commonly formed from silicon, glass, ceramics, plastics or metal.

Connection of capillary tubes (commonly having dimensions between 50 and 1000, desirably between 100 and 300 micrometers external diameter) to microengineered structures, especially those formed by bonding planar etched or formed substrates, generally requires low stress joining techniques. High temperature processes such as required to weld metals, ceramics, or glasses may generate damage such as substrate cracking or delamination. Within relatively thin (generally <2 mm) substrates, especially in ceramics or glass, the formation and maintenance of threaded, interference, or compression joints is not well established. Sealing of joints usually therefore requires use of sealing material.

In Reston & Kolesar "Silicon-Micromachined Gas Chromatography System—Part 1", Journal of Micromechanical Systems, IEEE/ASME, December 1994, page 139 there is shown a method of connecting a gas inlet tube to a gas chromatograph comprising a spiral flow path, 300 $\mu$m wide and 10 $\mu$m deep, etched into the surface of a silicon wafer substrate. A glass plate is bonded to the upper surface of the substrate over the spiral flow path, and a tapered gas feed through an aperture is formed in the lower surface of the silicon wafer communicating with the spiral flow path. An end of a gas inlet tube, 254 $\mu$m in diameter, is inserted into the tapered aperture, and an adhesive (epoxy resin) is applied around the end of the inlet tube and the open part of the aperture in order to seal the tube within the aperture.

There are a number of problems and disadvantages associated with such an arrangement where the capillary tubes enters the device perpendicular to the plane of substrates and the fluidic structures formed in those substrates. One problem is that having a capillary tube connection perpendicular to planar substrates and devices interferes with stacking of such substrates and devices to produce compact systems. Another problem is that formation of vias through substrates for connection of capillary tubes perpendicular to substrates can excessively complicate device fabrication and reduce achievable device density and yields. Formation of vias through substrates with near parallel or slightly tapered bores matched to capillary tube dimensions can be difficult. For structures etched in glass or silicon the masking and etch time requirements for the deep etching required for formation of such vias can be much more restrictive than those required for etching the fluidic channel structures into the substrate surface.

Another problem with such an arrangement is that the length of capillary tube enclosed within the substrate is limited to the thickness of the substrate, and that the length of adhesive bond supported intimately by the outer wall of the capillary tube and bore through the substrate is similarly limited to the thickness of the substrate. This can result in a relatively weak and fragile seal. Application of further adhesive around the capillary and onto the outer surface of the substrate may improve seal quality, but the improvement is often limited by poor bonding to planar substrate surfaces. Application of further adhesive around the capillary and onto the outer surface of the substrate may also be undesirable due to the resultant increase in unit volume and interference with packing together of units into a system. Similarly, bonding of conventional capillary connectors onto the substrate surface over a via may give poor seal quality, increase the area required for individual devices, and interferes with device packing and stacking.

Another problem with such arrangements is that feeding adhesive materials into the region between the capillary tube outer wall and the sides of the via bore sufficiently well to form a seal, but without adhesive entering and blocking or contaminating the fluidic channels and the capillary tube itself, can be difficult. It is generally necessary to use adhesive formulations of sufficiently high viscosity to prevent rapid flow of adhesive by capillary action into the fluidic channels. It is, however, generally difficult to observe or monitor and control how well the adhesive has fed into the via regions desired.

A further problem with such arrangement is, particularly for gases, that the fluid must flow into the microengineered structure in a direction perpendicular to the direction of the fluid channels within the structure and that the movement of the fluid through a right angle may create turbulence or other recirculating or mixin, processes and create flow conditions which are difficult to predict.

SUMMARY OF THE INVENTION

In a first aspect the present invention provides a method of connecting a capillary or other small bore tube to a microengineered structure to serve as a fluid flow port therefor, comprising: (1) providing a microengineered structure having at least a first planar substrate with fluid flow channels formed therein, the or each substrate having first and second opposite side surfaces extending substantially in the same direction as the plane of the or each substrate and end surfaces substantially normal to the plane of the or each substrate, and wherein an end surface of the at least one substrate has an aperture therein communicating with a said fluid flow channel; (2) providing a capillary tube or other small bore tube and inserting an end thereof into said aperture in said end surface; and (3) flowing within the aperture around the tube a sealant material, which is then hardened in order to seal the tube within the aperture.

The present invention provides in a further aspect apparatus comprising a microengineered structure having a fluid coupling, the structure comprising at least a first substrate with one or more fluid flow channels formed therein, the or each substrate being defined by first and second opposite side surfaces and end surfaces extending from the edges of the side surfaces, and including fluid inlet means comprising a capillary tube or other small bore tube inserted into an aperture formed in an end surface of the at least one substrate, which communicates with a said fluid flow channel, and wherein a sealant material is provided in the aperture, having been hardened in situ around the tube in the aperture subsequent to insertion of the tubing in the aperture.

In a further aspect, the invention provides a microengineered structure for a fluid coupling as set forth above wherein the structure comprises at least a first substrate with one or more fluid flow channels formed therein, the or each substrate being defined by first and second opposite side surfaces and end surfaces extending from the edges of the side surfaces, an aperture being formed in an end surface of the at least one substrate and communicating with a fluid flow channel and being dimensioned for receiving a capillary or other small bore tube.

The diameter of said aperture is sufficient to allow insertion of the tube (which may be 1000 micrometers diameter) together with sealant material around the tube, and may be different to the fluid flow channel diameter. Said aperture is such that the tube is positioned in the same plane and preferably the same direction as a fluid flow path of the structure, where the aperture is formed by a straight or gently curved guide channel running from a fluid flow channel to a substrate end surface.

As is common in microengineered structures, fluid flow channels may be formed in the surface of a first substrate, and a second substrate is stacked on the first substrate in order to seal the fluid flow channels. Alternatively the second substrate may have fluid flow channels formed in its lower surface which may communicate and co-operate with the flow channels in the upper surface of the first substrate. As an alternative arrangement, the fluid flow channels may be formed within the bulk of the first substrate, and a second substrate is not necessary for defining or sealing the fluid flow channels. In a further arrangement, the fluid flow channels and said aperture may be formed by building successive layers on top of an initial substrate, the substrate with such layers then defining said first substrate, with a second substrate preferably sealing the top of the fluid flow channels.

Fluidic channels on microengineered structures, and guide channels for tube connections when formed on and between plane substrates will not generally be of circular cross section to match the connecting tubes. Etched, milled or sawn channels may generally have cross sections of approximately semicircular, triangular, trapezoid, or rectangular forms. Superposition of semicircular channels in first and second substrates may yield approximately circular cross sections, but misalignment and deviations from symmetry of a few micrometers at least are to be expected. It is a requirement therefore that sealant for tubes connected into guide channels in the substrate plane must fill significant spaces around the tubes.

In accordance with the invention a means is provided of establishing a fluid flow connection to a microengineered structure, where the fluid may flow directly into the structure in a direction parallel with the fluid flow channels within the structure. Thus there is no turbulence or other unpredictable flow conditions created. Further, since the seal is created subsequent to insertion of the tube by addition or formation of a sealing material between the outer walls of the capillary tube and the inner wall of a channel section formed to contain the capillary tube, there is no excess pressures or thermal or other stresses created which might fracture the microengineering structure or cause a faulty seal.

An advantage of the invention is that the capillary tubes connect in the plane of the microengineered device allowing devices to be stacked. A further advantage is that the length of seal around the capillary tube within the device can be selected at the design stage without the constraint of the substrate thickness and can be made sufficient to assure a good seal. A further advantage where one or more substrates is transparent is that the extent of the seal can be observed and radiation curing low viscosity capillary filling sealant may be employed. A further advantage with some embodiments is that through vias do not need to be formed in the substrates. Where vias are proposed as described below for sealant feeding, they may be remote from the microengineered fluidic structures and need not be formed to the precision required for connectors perpendicular to the substrate.

In addition to providing external fluid connections to microengineered fluidic devices, a means is provided for linking fluid flow channels in separate microfluidic devices which may be on separate substrates or may share one substrate or may be on a series of overlapping substrates bonded together.

The sealant material may comprise a substance, or mixture of substances, as will become clear below. The sealant material will be selected from substances such as adhesives or cementing materials. These most generally will be organic materials such as epoxy resins, but may include other polymeric or polymerisable materials including inorganic materials or components.

In one preferred embodiment, the seal is formed by a method as described and claimed in our European Patent Number EP-B-319175 (our Ref PA1314); the patent describes and claims a method of forming a solid article of predetermined shape from a liquid which can be cured by exposure to radiation, the method comprising the steps of providing a surface upon which the article is to be formed; exposing a predetermined region of the surface to a beam of radiation; supplying the liquid to an unexposed region of the surface such that a solid barrier, defining a surface of the solid article, is created at the interface of the liquid and the beam, and curing the liquid which has been supplied but not yet cured to form said solid article.

Thus to apply such a method to the present invention, a microengineered structure with fluidic channels in the substrate plane is fabricated with fluidic channels connecting as desired with straight or gently curved guide channels also in the substrate plane which run to a substrate edge. The cross section of the guide channels is large enough to allow tube insertion at the aperture formed at a substrate edge and for the capillary tube to be fed into the structure to connect with the fluidic channels. A beam of, for example, ultra violet radiation is applied through a transparent substrate material adjacent to the end of a capillary tube positioned within an end aperture in a microengineered structure at the end limits of the desired position of the sealing substance. A radiation curing sealing substance is then fed into the open end of the guide channel so that the liquid sealant flows around the tube and into the aperture. The flow of liquid sealant may be driven by hydrostatic or other applied pressure or by capillary forces or a combination of these forces. When it reaches the beam of radiation, it is hardened and cured. When a solid plug is created at the end, the beam may then be moved through the uncured substance so as to create a completely hardened plug. Alternatively, the remainder of the substance may be cured by broad exposure to UV or light, or by the application of heat.

BRIEF DESCRIPTION OF THE DRAWINGS

Preferred embodiments of the invention will now be described with reference to the accompanying drawings wherein:

FIG. 3 is a schematic side sectional view showing the method by which a second fluid coupling of FIG. 1 is formed;

FIGS. 4 and 5 are schematic side sectional views of the second fluid coupling of FIG. 1 and a modification thereof;

FIGS. 7 and 8 are schematic side sectional views of methods of forming respective second and third embodiments of the invention;

FIGS. 9–12 are schematic side sectional views of methods of forming respective fourth to seventh embodiments of the invention.

DESCRIPTION OF THE PREFERRED EMBODIMENTS

Figure 1:
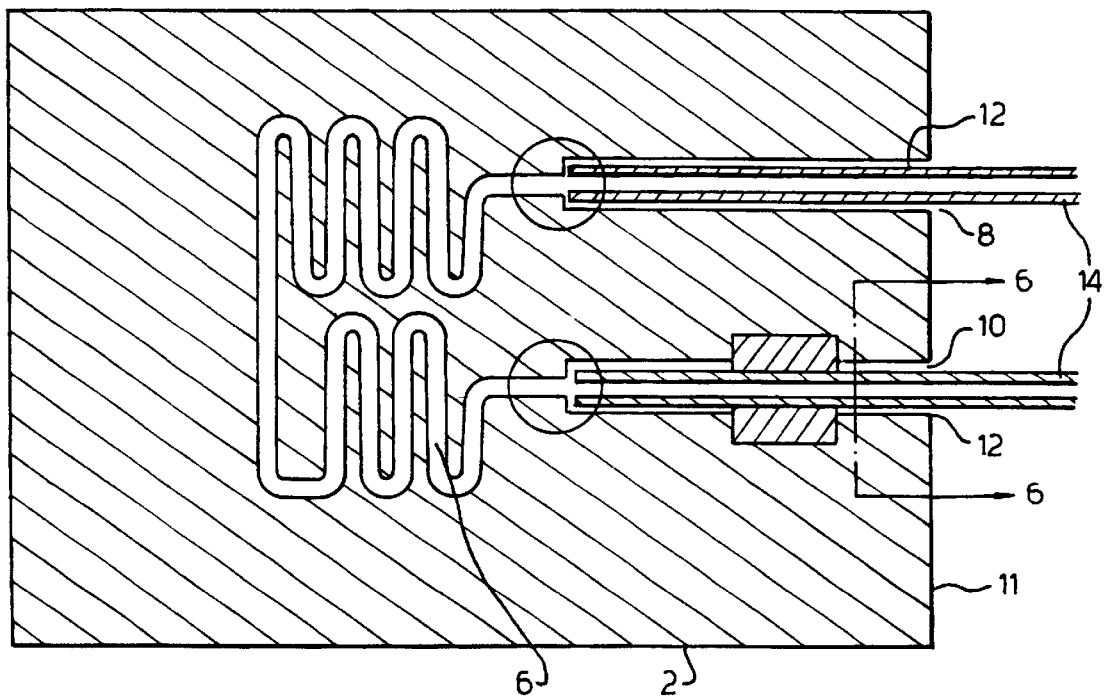
FIG. 1 is a schematic plan view of a microengineered structure according to the invention with first and second fluid couplings providing input and output ports.

Referring now to FIG. 1 to 6, there is shown a microengineered structure comprising a first silicon substrate 2 and a second glass substrate 4 (FIG. 6) positioned face to face with the first substrate. The substrate 2 is defined by upper and lower opposite side surfaces and end surfaces extending from the edges of the side surfaces. First substrate 2 has a serpentine fluid flow channel 6 formed in the upper surface thereof extending from an inlet port 8 to an outlet port 10, both formed in an end surface 11 of the substrate. It will be understood that the fluid flow channel may take various forms, depending upon the application, for example, large area chambers etc. Fluid flow channel 6 has a diameter, width or thickness less than 1000 micrometers, typically 100 micrometers, and may be of any suitable shape, for example triangular cross section.

Fluid inlet port 8 and fluid outlet port 10 are both formed with apertures 12 formed in end surface 11 and having the form of bores, having a width, as shown more than twice that of channel 6. Apertures 12 receive capillary tubes 14 which may have a variety of sizes, for example 300 micrometers external diameter, 200 micrometers internal diameter, or 200 external, 150 internal, or 100 external 50 micrometers in diameter. The cross sectional shape of bores 12 may take a variety of forms as shown in FIG. 6 namely (a) triangular, (b) truncated triangular, (c) semi circular, (d) rectangular, and (e) circular. It will be noted that in FIG. 6 all of the bores 12 are formed in the upper surface of substrate 2 apart from the circular bore of FIG. 6e which is formed partly in substrate 2 and partly in the lower surface of substrate 4, but in general the bore could be formed in either substrate. An alternative construction is shown in FIG. 6f and 6g wherein a circular bore is formed wholly within substrate 2 by an etching technique involving cutting a vertical slit 19 in the upper surface of substrate 2 and then generating a circular bore by an etching technique. The slit will be sealed with sealant material 18 in the finished form of the fluid coupling, as shown in FIG. 6g.

Figure 6A:
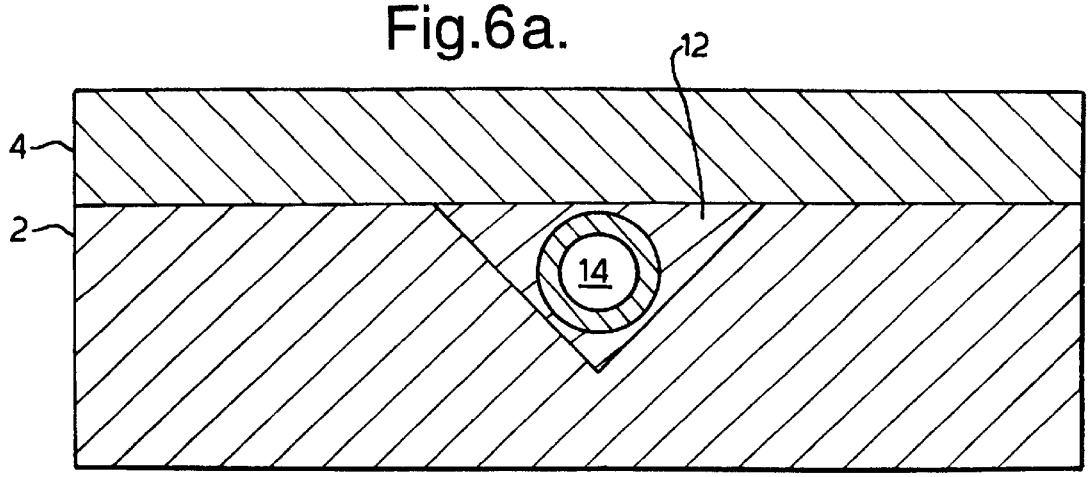
FIGS. 6a–6h are cross sectional views along the line 6—6 of FIG. 1 for various cross sections of fluid flow channels.
Figure 6B:
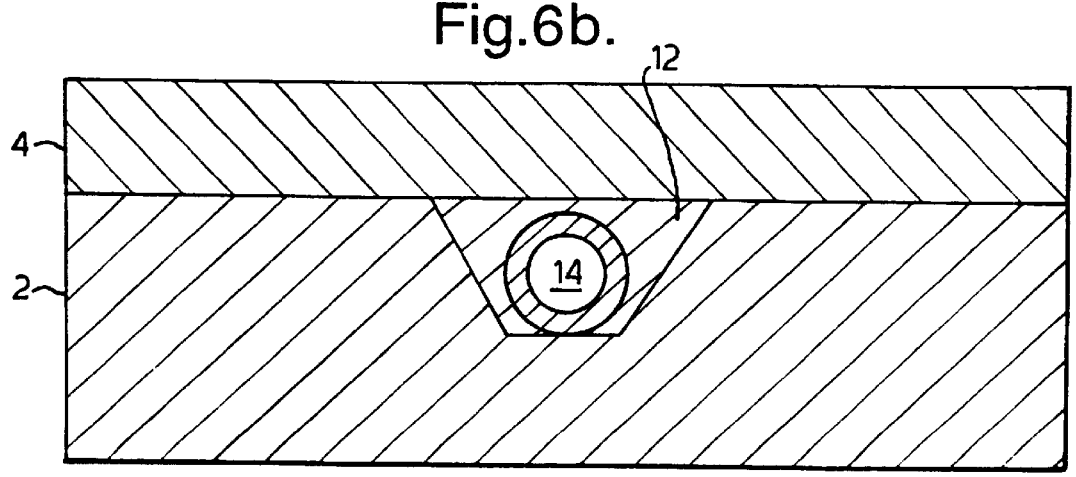
Figure 6C:
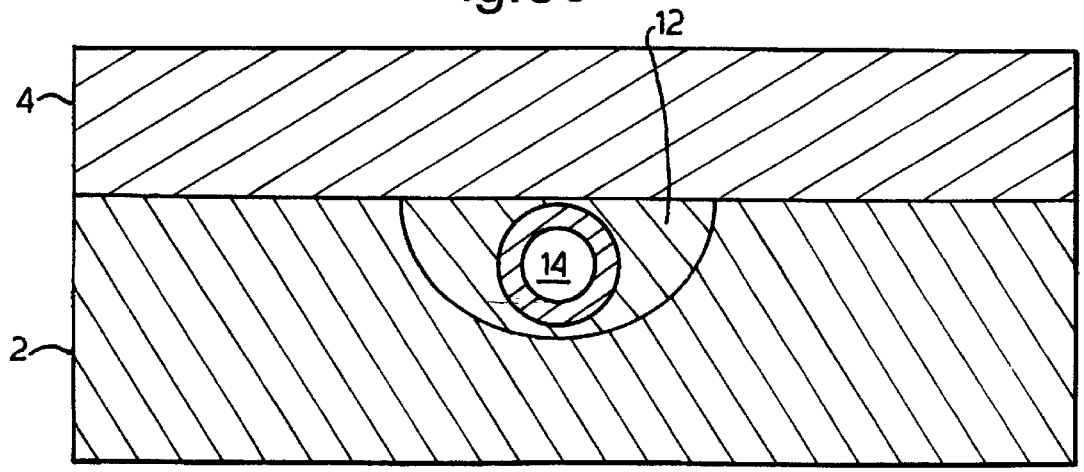
Figure 6D:
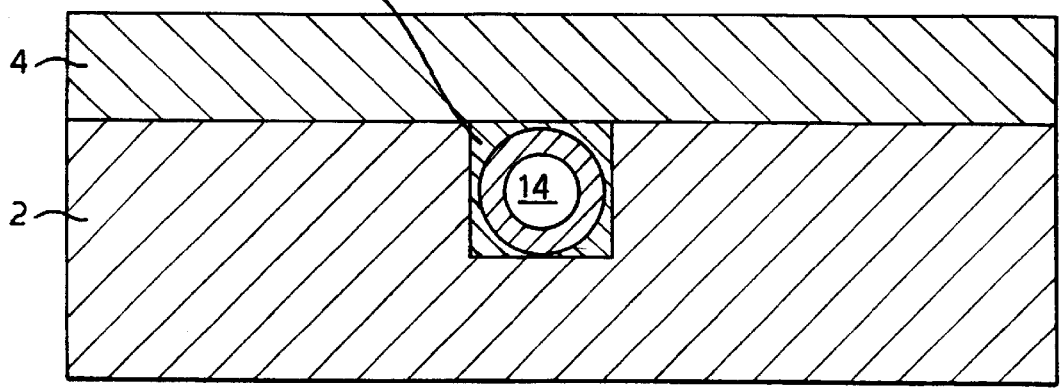
Figure 6E:
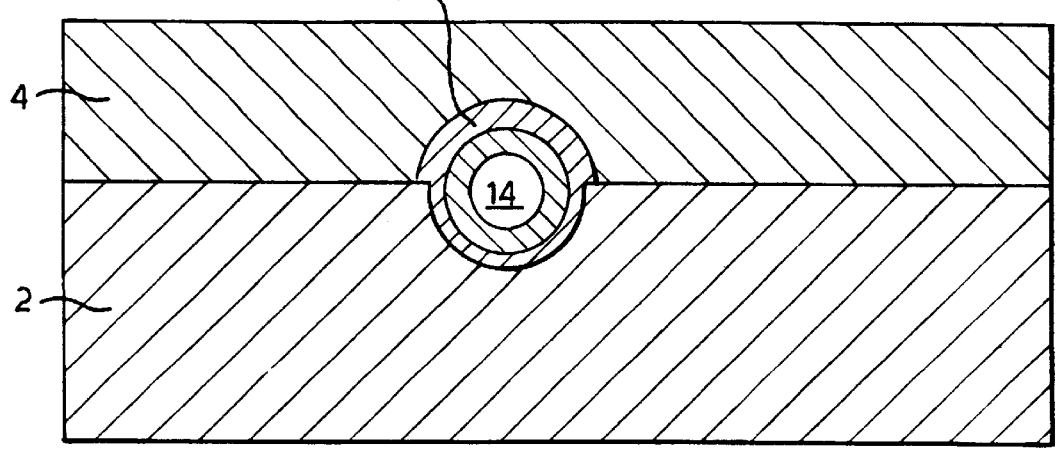
Figure 6H:
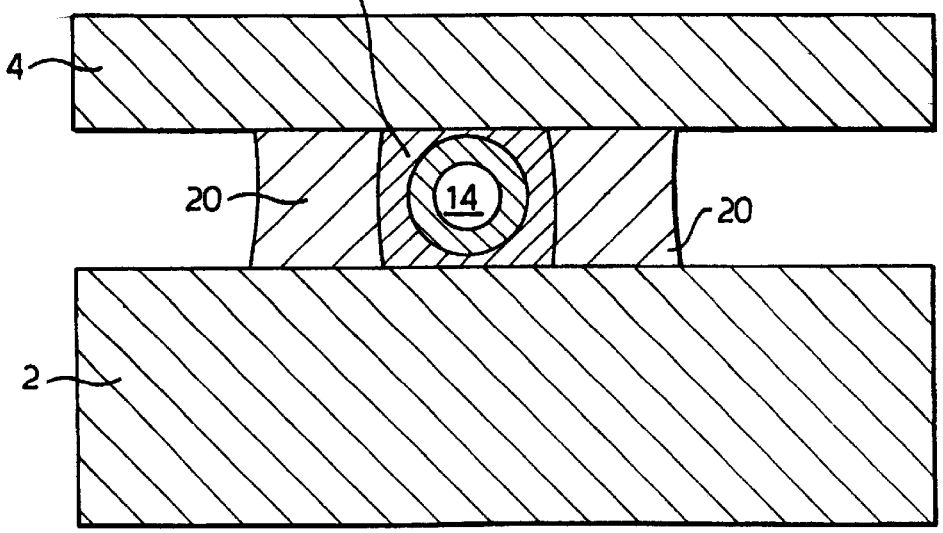
Figure 6F:
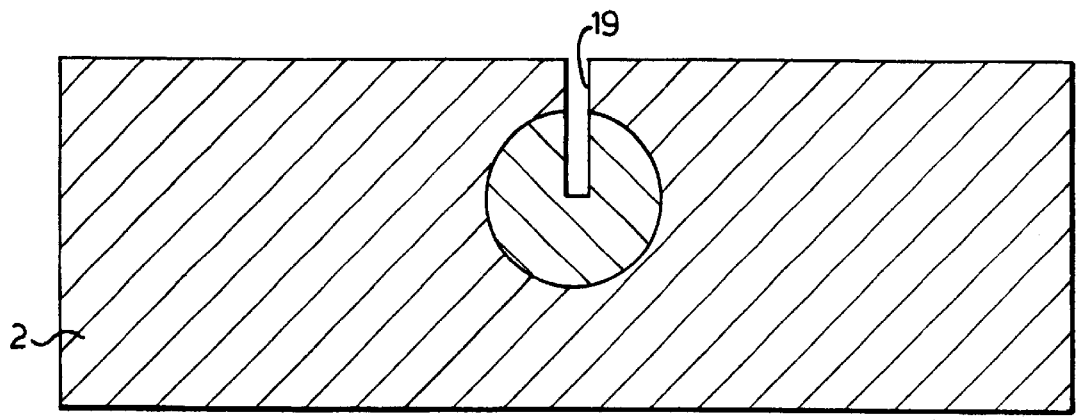
Figure 6G:
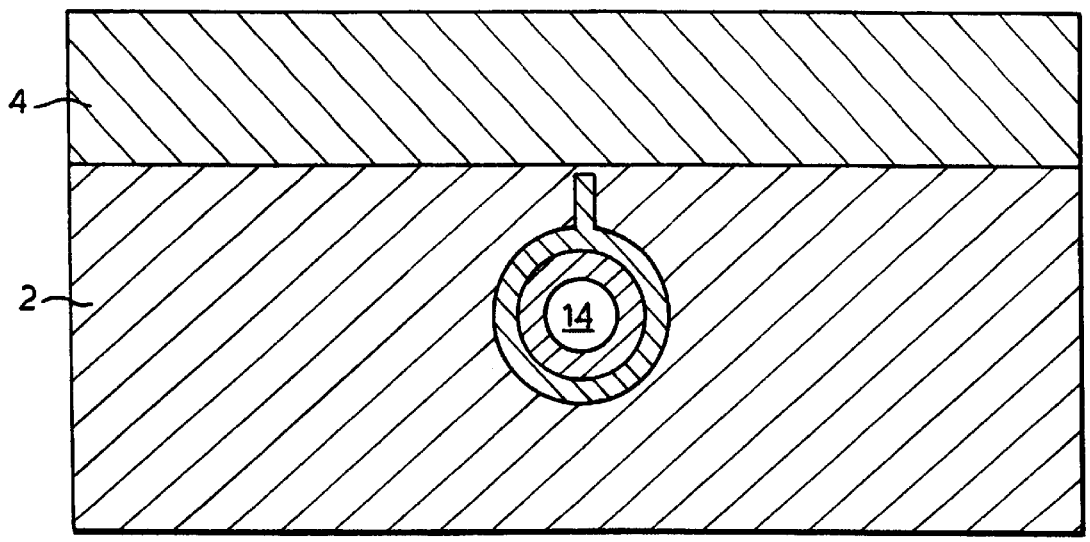

In FIG. 6h an alternative construction is shown wherein bore 12 and fluid flow channels 6 are formed on the upper surface of base substrate 2 by building, by any suitable microengineering technique (defined by printing, photolithography, lamination, and modified by etching if required), layers 20 which define the side walls of the bore and fluid flow channels. The lower surface of the bore is defined by the upper surface of base substrate 2 and the upper surface of the bore is defined by the lower surface of substrate 4 which is subsequently bonded to layers 20. In such an arrangement, the upper surface of the layers 20 define, in part, the upper surface of said first substrate.

Figure 2:
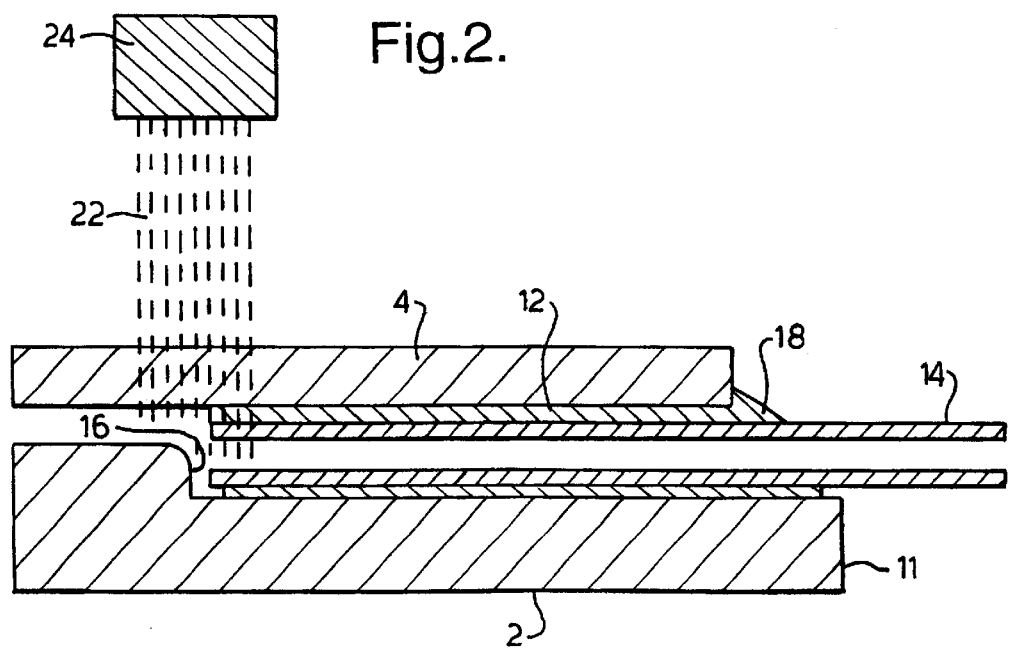
FIG. 2 is a schematic side sectional view showing the method by which a first fluid coupling of FIG. 1 is formed.

For the sake of explaining the invention, the fluid coupling to inlet port 8 is formed differently from that to outlet port 10. Referring to FIG. 2 which shows the method of forming the fluid coupling with inlet port 8, capillary tube 14 is first inserted in to bore 12 close to a point where bore 12 merges with flow channel 6 at a shoulder 16. Capillary tube 14 may be formed of silica, but may be glass, polymer or even metal. A radiation curable material 18 is flowed into the open end of bore 12 and is such as to wick along bore 12 towards the end of tube 14. A beam of ultra violet radiation 22 is directed at the end of tube 14 from a light source 24 through transparent glass substrate 4 so that when the liquid reaches the beam it is hardened. Once a solid plug has been formed at the end of the tube 14, the light source may be moved along the length of the tube so as to cure and harden the remainder of liquid 18. Alternatively a second light source (not shown) is provided for general exposure of the liquid 18.

In a variation of the method as shown in FIG. 3 which is adopted for outlet port 10, a through aperture or via 30 is provided into which the radiation curable material is flowed. Otherwise the method is similar to that shown in FIG. 2. The advantage of having a separate inlet via 30 for the radiation curable material is where the material is not sufficiently fluid to permit it to be flown from the end of fluid inlet port 8.

Referring to FIGS. 4 and 5, it is necessary when flowing material into the fluid inlet port 8 to avoid injection of excess material, which may flow into the fluid flow channel 6 and block the channel. Control is usually exercised by physical observation of the amount of material injected. In FIG. 4, a via 30 is positioned approximately mid way between the open end of the bore and fluid flow channel 6. When sealant material starts emerging from the open end of the bore, as shown by swelling 40, an observer will know that the material has also reached the inner end of tube 14, and that further injection of material should be stopped.

In FIG. 5 an alternative arrangement is shown for injecting a smaller amount of material, wherein a second via 50 is provided communicating with the bore and positioned adjacent to via 30. During inflow of sealant material through via 30, an observer observes the ingress of sealant material into via 50, as shown by swelling 52, and at that point will appreciate that a sufficient amount of sealant material has been inserted and has reached the inner end of tube 14.

The radiation curing material may most generally be a UV or light curing polymeric material. A variety of UV curing acrylic materials with a range of viscosities are available commercially (Norland UV Sealants, Norland Products Inc., New Brunswick, N.J. 08902, USA) and examples from that range ( e.g. high viscosity Norland 91, low viscosity Norland 81) or similar materials may be selected for use in the methods described below where one or more of the substrate materials is transparent to the radiation.

Feeding sealant into the aperture at a substrate edge is particularly convenient for low viscosity sealant which feeds into the guide channel by capillary action. For such low viscosity sealant it is necessary to provide a means of curing the sealant at the desired position in the guide channel by, for example, UV radiation so as to prevent the sealant running beyond the tube end and into the tube and the fluidic structure. For sufficiently viscous sealant, where flow is only significant under applied pressure, curing may also be by radiation, but use of non-radiation curing sealant is also possible. Where a sufficiently viscous sealant, especially a viscoelastic formulation, is employed such that flow within the guide channel is insignificant under capillary action but may be produced by pressure applied to the sealant at the aperture at a substrate edge, or by vacuum applied within the microengineered structure, flow may be stopped by removing the pressure differential and the sealant cured or allowed to cure. An example is high viscosity two part epoxy which may be applied in e.g. Ciba Geigy Araldite 2005. The removal of the pressure differential may be in response to observation of the sealant front in the guide channel, or by observing sealant extruding from the channel, possibly automated with the aid of a vision system, or after a known time determined to produce the required amount of flow. The arrangements of FIGS. 4 and 5 would be particularly suitable.

Where sufficient thermal control can be applied to parts of the structure, a molten sealant material may be used which solidifies at the desired position within the guide channel.

Referring to FIG. 7 and 8, these show a modification of the method of FIG. 4 wherein an insert rod member 70 is inserted into tube 14 so as to project beyond the end thereof into fluid flow channel 6. In FIG. 7, bore 12 and channel 6 are formed equally in substrate 2 and substrate 4, whereas in FIG. 8, bore 12 and channel 6 are formed wholly in substrate 2. FIGS. 7 and 8 show a method for allowing sealant to go beyond end of the tube and reduce dead space. The insert 70, e.g. rod, fibre (possibly optical), wire, or narrower tube, is passed through tube 14 and into fluid channel 6. The sealant is allowed to flow beyond end of connection tube 14 and around insert 70 before curing. The insert is removed by pulling out (e.g. for tungsten wire, or optical fibre, possibly coated with release agent), or melting (e.g. for polypropylene or PMMA fibre or rod, or Indium wire), or dissolving (e.g. for Cu or Ni tubes).

Referring now to the embodiment shown in FIG. 9, the substrates 2, 4 are of an opaque material. To permit the use of radiation ( e.g. UV) curing sealant, the radiation beam 90 is carried into the structure by an optical fibre 92 which is passed inside tube 14 which is transparent. Alternatively, the fibre could be passed through the flow channels 6. Thus the coupling is formed as described above with reference to FIG. 2 but with the fibre optic 92 inserted in the tube 14 and positioned so that the region 94 at the end of the tube is bathed in radiation. Radiation curing sealant 18 flows up the guide channel towards the end of the tube and is cured by the radiation, thus preventing sealant passing into tube and fluidic channels. After forming a plug in region 94, the fibre optic is withdrawn slowly irradiating the rest of the sealant through the tube wall.

Figure 10:
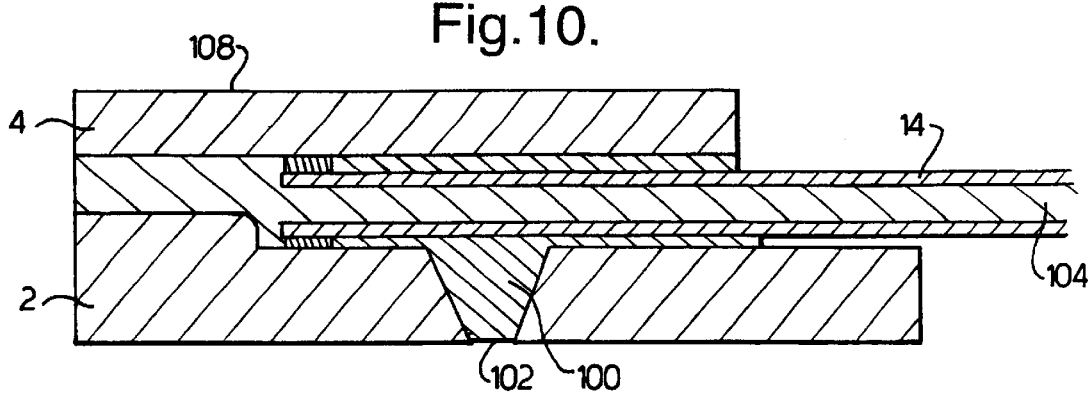

Referring now to FIG. 10, this shows a method for precipitant sealing by flowing two liquids into the system which react to form a solid. Thus, for example, concentrated viscous sodium silicate solution 100 is fed in though via 102, while a much less viscous solution 104 of for example a calcium or magnesium salt (e.g. $CaCl_2$) is fed in through tube 14. An insoluble silicate precipitate is formed at region 108 at the end of the tube. By adjusting concentrations and flow rates it is ensured that the precipitate remains in bore 12 around tube and progressively gets denser as $Ca^{2+}$ ions diffuse into the silicate, while any precipitate formed in the solution flowing through the centre of tube 14 gets swept away by force of flow.

Figure 11:
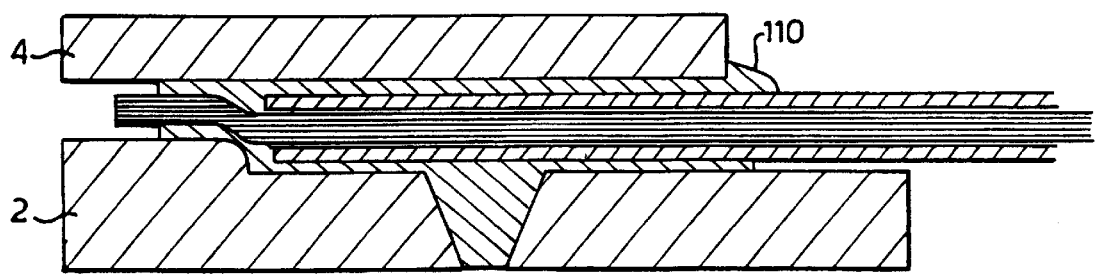
Figure 12:
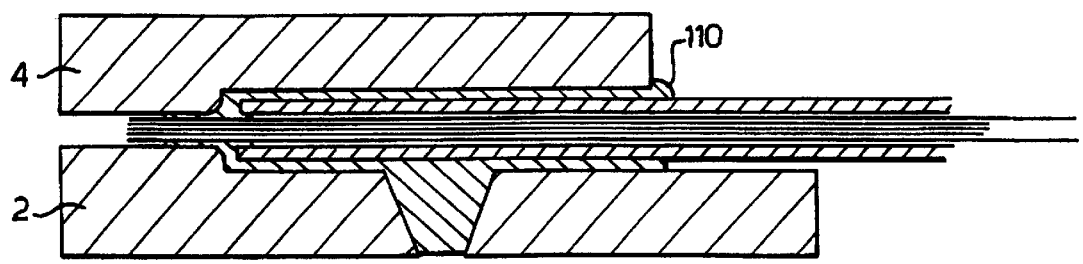

Referring to FIGS. 11 and 12, these are similar to FIGS. 7 and 8 except that both substrates 2, 4 are opaque and it is therefore necessary to use a viscous, preferably viscoelastic material 110 which can be injected into via 30 under pressure and which sets upon the release of pressure and/or the application of heat.

In a further modification (not shown), of FIGS. 7 and 8, the capillary tube is dispensed with, and the sealing material is grown on the outside of aperture 12 so as to boss onto which an external connection may be made.

Figure 13A:
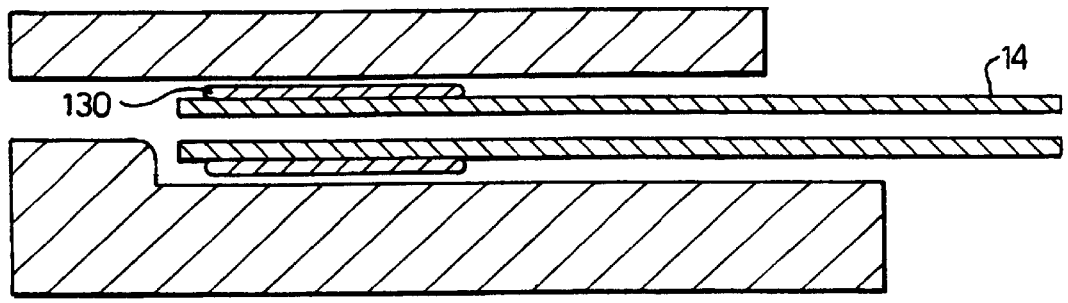
FIGS. 13a–13c are views illustrating a method in accordance with an eighth embodiment of the invention.
Figure 13B:
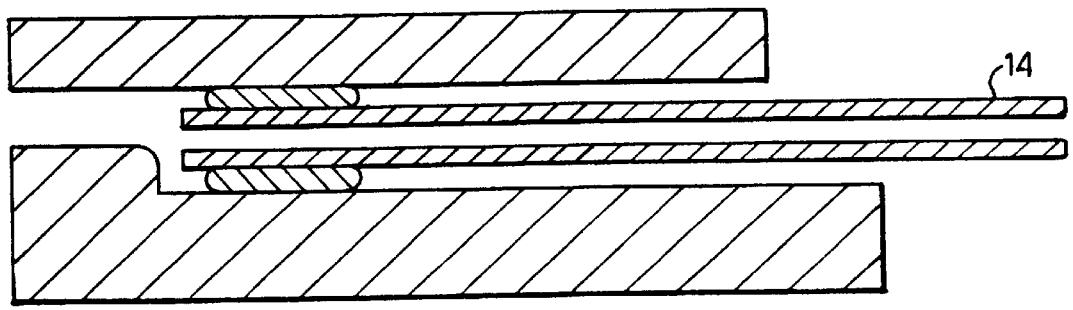
Figure 13C:
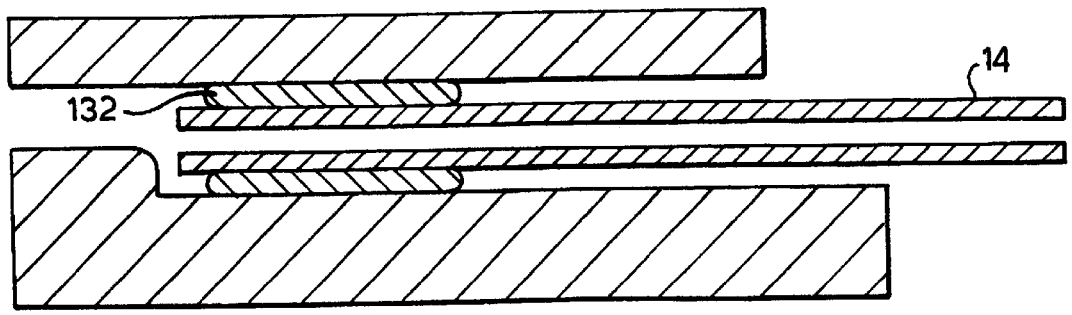

Referring now to FIGS. 13a to 13c, these show an eighth embodiment of the invention wherein a tube 14 has a preformed sleeve insert 130 formed around its inner end and of an external diameter less than that of bore 12. This allows free insertion of tube 14 within the bore as shown in FIG. 13a. When fully positioned in the bore, heat is applied which causes the insert material to melt and form a seal between the tube 14 and the inner walls of the bore 12 as shown in FIG. 13b.

In FIG. 13c, a sleeve insert material material 132 is provided which expands after insertion by application of a chemical reactant to change the composition of the material, e.g. iron expanding to iron oxide. Upon the removal of heat, the sealant material remains in the position shown in FIG. 13c.

It will be appreciated that in the embodiments of FIG. 13 and 10, in particular, that where a plug is formed at the end of the tube, the remainder of the bore may subsequently be filled with a sealant material injected and hardened in accordance with any of the other embodiments, for example that in FIG. 2.

In addition, alternative sealants to radiation curable sealants may be employed. For example, an anaerobic curing sealant which cures within the bore around the tube could be used, in which case sufficient control on the sealant flow rate and/or cure time is needed, and also, possibly a flush device with nitrogen or other oxygen free gas. Alternatively the sealant material could be a viscous ceramic cement inserted by way of a via, as described with reference to FIG. 3. Example of such ceramic cements are Portland cement, plaster of Paris paste (hydrating gypsum $CaSO_4$), or phosphate cement (e.g., based on aluminium orthosposphate solution and MgO.

What is claimed is:

1. A method of providing a fluid connection between a tube and a micro-engineered structure to serve as a fluid flow port therefor, comprising:

providing a micro-engineered structure having at least one substrate with at least one fluid flow channel formed therein, said at least one substrate being defined by a first side surface and a second side surface and a plurality of end surfaces extending from edges of said first side surface and said second side surface, and at least one of said plurality of end surfaces of said at least one substrate having therein an aperture in communication with said at least one fluid flow channel;

inserting a tube in said aperture of said at least one of said plurality of end surfaces; and allowing a sealant material to flow within said aperture around said tube, said sealant material being allowed to harden to provide a seal between said tube and said at least one of said plurality of end surfaces within said aperture.

2. The method of providing a fluid connection in accordance with claim 1, wherein:

said tube is a capillary tube.

3. The method of providing a fluid connection in accordance with claim 1, further comprising:

directing a beam of radiation at an inner end of said tube within said aperture;

wherein said sealant material comprises a radiation curable material, said sealant material being hardened upon exposure to said beam of radiation as said sealant material is introduced into said aperture.

4. The method of providing a fluid connection in accordance with claim 3, further comprising:

moving said beam of radiation along said tube to harden said sealant material within said aperture once a solid plug is formed at said inner end of said tube.

5. The method of providing a fluid connection in accordance with claim 4, wherein:

said at least one substrate is made of a transparent material; and said directing said beam of radiation step includes directing said beam of radiation at said sealant material through said at least one substrate.

6. The method of providing a fluid connection in accordance with claim 4, wherein:

said tube is made of a transparent material; and said directing said beam of radiation step includes directing said beam of radiation at said sealant material through said tube.

7. The method of providing a fluid connection in accordance with claim 1, wherein:

said sealant material is viscous, and allowed to flow into said aperture under pressure, said sealant material being hardened upon subsequent removal of said pressure.

8. The method of providing a fluid connection in accordance with claim 7, wherein:

said sealant material is viscoelastic.

9. The method of providing a fluid connection in accordance with claim 1, wherein:

said sealant material is inserted into said tube in a molten form, and hardened by subsequent cooling of said sealant material.

10. The method of providing a fluid connection in accordance with claim 1, wherein:

said sealant material is a cement inserted into said aperture in a fluid form, and subsequently hardened.

11. The method of providing a fluid connection in accordance with claim 1, wherein:

said sealant material comprises at least a first substance introduced in said aperture and a second substance introduced through said tube, said first and said second substances mixing and reacting together at an inner end of said tube to create a seal within said aperture around said tube.

12. The method of providing a fluid connection in accordance with claim 1, further comprising:

forming a cylindrical insert on an end of said tube, an external dimension of said cylindrical insert permitting free insertion of said tube in said aperture; and melting said cylindrical insert when said tube is inserted in said aperture to seal said tube to an inner surface of said at least one of said end surfaces within said aperture.

13. The method of providing a fluid connection in accordance with claim 1, further comprising:

forming a via in said at least one substrate, said via permitting said sealant material to flow therethrough to said aperture.

14. The method of providing a fluid connection in accordance with claim 1, wherein:

an amount of said sealant material allowed to flow into said aperture is determined by physical observation of said sealant material within said aperture.

15. The method of providing a fluid connection in accordance with claim 13, further comprising:

providing a further via in said at least one substrate to permit observation of said sealant material flowing along said aperture and into said further via, said observation allowing a determination whether sufficient material has flowed into said aperture.

16. The method of providing a fluid connection in accordance with claim 1, further comprising:

inserting a rod member through said tube into said at least one fluid flow channel in order to permit said sealant material to flow into said aperture as close as possible to said at least one fluid flow channel without blocking said at least one fluid flow channel; and withdrawing said rod member from said tube subsequent to hardening of said sealant material.

17. The method of providing a fluid connection in accordance with claim 1, further comprising:

forming said aperture with a straight guide channel running from said at least one fluid flow channel to said at least one of said plurality of end surfaces.

18. The method of providing a fluid connection in accordance with claim 1, further comprising:

forming said aperture with a curved guide channel running from said at least one fluid flow channel to said at least one of said plurality of end surfaces.

19. The method of providing a fluid connection in accordance with claim 1, further comprising:

forming said aperture with a bore running from said at least one fluid flow channel to said at least one of said plurality of end surfaces.

20. A method of providing a fluid flow port on a micro-engineered structure for allowing external fluid connection thereto, comprising:

providing a micro-engineered structure having at least one substrate with at least one fluid flow channel formed therein, said at least one substrate being defined by a first side surface and a second side surface and a plurality of end surfaces extending from edges of said first side surface and said second side surface, and at least one of said plurality of end surfaces of said at least one substrate having therein an aperture in communication with said at least one fluid flow channel;

growing a sealant material on an outside of said aperture to provide a structure, said structure allowing an external fluid connection thereto.

* * * * *